| United States Patent [19] | [11] Patent Number: 4,853,328 |
|---|---|
| Okazaki et al. | [45] Date of Patent: Aug. 1, 1989 |

[54] REAGENT FOR ASSAYING HYDROGEN PEROXIDE AND METHOD OF QUANTITATIVE ASSAY FOR HYDROGEN PEROXIDE

[75] Inventors: Masaki Okazaki; Yoshio Inagaki, both of Kanagawa, Japan

[73] Assignee: Fuji Photo Film Co., Ltd., Kanagawa, Japan

[21] Appl. No.: 862,195

[22] Filed: May 9, 1986

Related U.S. Application Data

[63] Continuation of Ser. No. 357,938, Mar. 15, 1982, abandoned.

[30] Foreign Application Priority Data

Mar. 13, 1981 [JP] Japan ................................. 56-36050

[51] Int. Cl.$^4$ .......................... C12Q 1/28; C12Q 1/26; G01N 33/535
[52] U.S. Cl. .......................................... 435/28; 435/7; 435/25; 435/805; 435/810
[58] Field of Search ...................... 435/7, 28, 25, 805, 435/810

[56] References Cited

U.S. PATENT DOCUMENTS

| 2,680,746 | 6/1954 | Schäppi | 549/289 |
|---|---|---|---|
| 3,351,482 | 11/1967 | Raue | 549/289 |
| 4,269,938 | 5/1981 | Frank | 435/14 |
| 4,558,130 | 12/1985 | Buckler et al. | 435/28 |

FOREIGN PATENT DOCUMENTS

| 1186078 | 1/1965 | Fed. Rep. of Germany | 549/289 |
|---|---|---|---|
| 2034306 | 1/1972 | Fed. Rep. of Germany | 549/289 |
| 47390 | 11/1972 | Japan | 549/289 |

OTHER PUBLICATIONS

March Advanced Org. Chem. Reactions, Mechanisms and Structure McGraw-Hill Book Co. 1977.
Kirkiacharian (I) CA. 48122s. vol. 75. 1971, Kirkiacharian (II) CA 82102e vol. 67, 1967.
Gold et al. CA. 92:22338t 1980.
Weinstein et al., Chemical Abstracts, 92:22337s, p. 668–669 (1980), "Synthesis of Quaiacylglycol and Glycerol-$\beta$-O-($\beta$-Methylumbilliferyl)ethers:lignin Model Substrates for Possible Fluorometric Assay of $\beta$-Etherases".
Barman, *Enzyme Handbook*, vol. I, Springer-Verlag, New York, NY., 234–235 (1969).

*Primary Examiner*—Esther M. Kepplinger
*Attorney, Agent, or Firm*—Sughrue, Mion, Zinn, Macpeak, and Seas

[57] ABSTRACT

A reagent suitable for assaying a very small amount of hydrogen peroxide is composed of a moiety having a residue formed by removing one hydrogen from an active methylene group or an active methine group and a fluorescing moiety.

Hydrogen peroxide contained in a sample liquid is determined by reacting the sample with the foregoing reagent, a hydrogen donor, and peroxidase and measuring the intensity of the fluorescence emitted from the fluorescing material formed by the reaction.

5 Claims, 1 Drawing Sheet

REAGENT FOR ASSAYING HYDROGEN PEROXIDE AND METHOD OF QUANTITATIVE ASSAY FOR HYDROGEN PEROXIDE

CROSS REFERENCE TO RELATED APPLICATION

The present application is a continuation of U.S. application Ser. No. 357,938 filed Mar. 15, 1982, which is now abandoned.

BACKGROUND OF THE INVENTION

1. Field of the Invention

This invention relates to a novel reagent for assaying hydrogen peroxide wherein peroxidase acts as a catalyst or takes part in the assay and also a method of quantitative assay for hydrogen peroxide.

2. Development of the Invention

Recently, the specificity of an enzymological analytical method in clinical inspection is highly evaluated and the analytical method is rapidly spreading. As the analytical method of measuring urine and glucose, uric acid, cholestrol, triglyceride, lactic acid, creatinine, free fatty acid, glutamylpyruvate transminase, glutamyloxalacetate transaminase, cholinesterase, creatine phosphokinase, lactic acid dehydrogenase, etc., in body fluid, a method of assaying a desired material by assaying hydrogen peroxide formed by reacting an oxidase acting on a material to be finally assayed in each system with the material has been frequently used.

As conventional methods for assaying hydrogen peroxide, there are known a method of converting a chromogen such as o-tolidine, 2,7-diaminofluorenone, N,N-dimethyl-p-phenylenediamine, o-dianisidine, o-aminophenol, triarylimidazoles, etc., into a colored material of an oxidized form and colorimetrically measuring the colored material, a method for oxidative-coupling of a combination of 4-aminoantipyrine and phenol, an N,N-dialkylaniline or an N,N-dialkyltoluidine, a combination of 3-methyl-2-benzothiazolinonehydrazone and o-tolidine, N,N-dimethylaniline or N,N-diethylaniline; or a chromogen such as 4-methoxy-1-naphthol forming a dimer and a derivative thereof, to form a colored material and colorimetrically measuring the colored material, etc. However, in such colorimetric method, there is a limitation on the assaying sensitivity and it is impossible by such conventional colorimetric methods to determine a very small amount of hydrogen peroxide.

Also, as a determination method by a fluorescent method, there is known a method of using homovanillic acid but it is very difficult to determine a very small amount of hydrogen peroxide by such an assay method. For overcoming the difficulty, a method of using fluorescin is proposed as is disclosed in Japanese patent application (OPI) No. 43791/79 (the term "OPI" as used herein refers to a published unexamined Japanese patent application.) but since fluorescin has a hydroquinone-like structure and hence is liable to be oxidized, there is a problem on the stability of the method. As an improvement for the method, a method of using diacetylfluorescin is proposed as is disclosed in Japanese patent application (OPI) No. 48656/80. However, in the case of using the compound, its preferred pH range is 7.5 to 9.5, which differs from the optimum pH for glucose oxidase and cholesterol oxidase. Therefore, the development of reagents which are stable and can be used for the determination of hydrogen peroxide in a low pH region.

SUMMARY OF THE INVENTION

Thus, an object of this invention is to provide a stable reagent capable of determening hydrogen peroxide in a low pH region.

Another object of this invention is to provide a determination method for hydrogen peroxide using the foregoing reagent.

As a result of various investigations on fluorescing reagents for assaying a very small amount of hydrogen peroxide wherein peroxidase acts as a catalyst or takes part in the determination, the inventors have discovered that the above-described objects of this invention can be effectively attained by a reagent for assaying hydrogen peroxide comprising a moiety having a residue formed by removing one hydrogen atom from an active methine and a fluorescing moiety, and also by a method of assaying hydrogen peroxide which comprises reacting a smaple containing hydrogen peroxide with the foregoing reagent for assaying hydrogen peroxide, a hydrogen donor, and peroxidase and measuring the intensity of the fluorescence emitted from the fluorescing material formed by the reaction.

DESCRIPTION OF THE PREFERRED EMBODIMENTS

Figure 2:
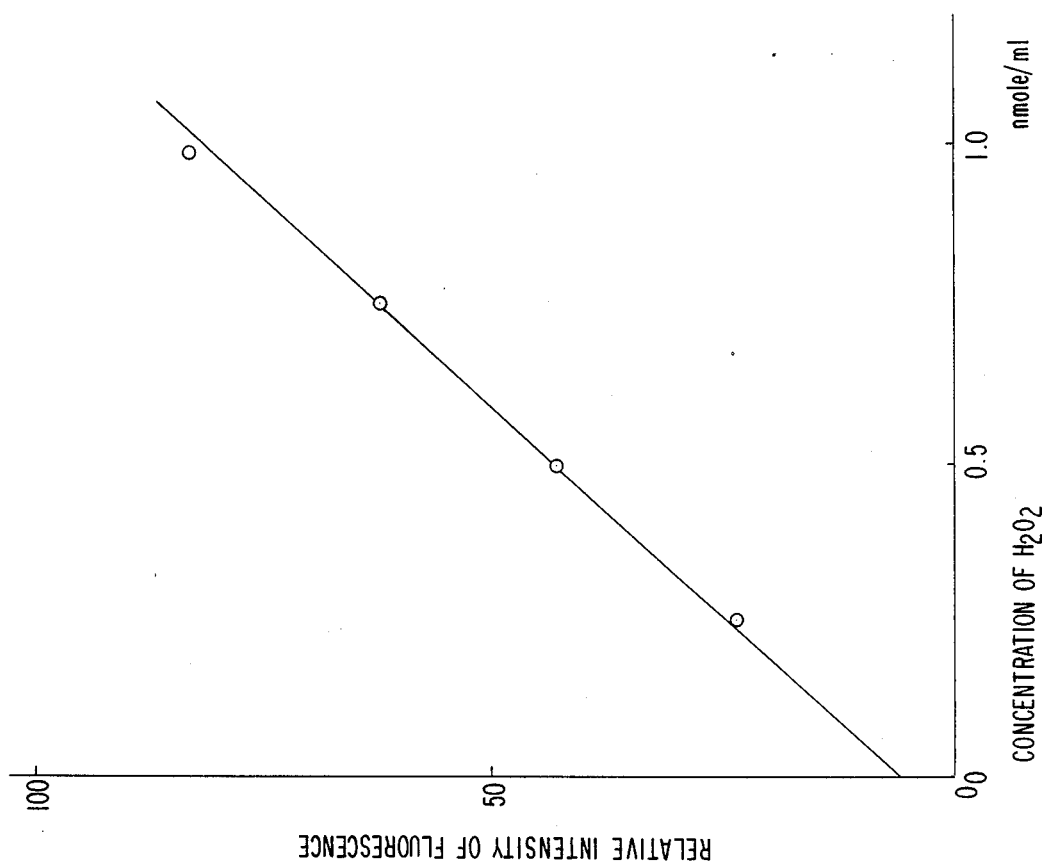

The reagent for assaying hydrogen peroxide of this invention is preferably a compound shown by formula (I):

$$Q-Fl \qquad (I)$$

wherein Q represents a moiety having a residue formed by removing one hydrogen atom from an active methylene group or an active methine group; said Q being bonded to Fl by the active methylene residue or the active methine residue therein; and Fl represents a moiety capable of emitting fluorescence by being separated from Q.

Now, the term "active methylene group" or "active methine group" as used in this invention refers to a methylene group or methine group capable of releasing a proton by the action of a base and practical examples of the active methylene group or active methine group are methylene groups or methine groups each having directly or indirectly (through, for example, a conjugated double bond) an electron withdrawing or attractive group such as carbonyl group, a cyano group, a halogen atom, a sulfonyl grup, a sulfoxide group, a nitro group, an imino group, etc.

In the case of measuring a material forming hydrogen peroxide by the action of an oxidase, hydrogen peroxide formed can be determined further using an oxidase in combination with the above-described three kinds of the effective components (i.e., a reagent for assaying hydrogen peroxide, a hydrogen donor and a peroxidase); further, a material to be determined can directly be assayed by utilizing a calibration curve or calculation formula of the material prepared in term of hydrogen peroxide.

In the case of assaying, for example, chemical materials contained in a body fluid or urine, the quantitative analysis of uric acid, glucose, cholesterol, etc., can be performed using uricase, glucose oxidase, cholesterol oxidase, etc., respectively, as the oxidase.

The quantitative analysis of such chemical materials is particularly important in clinical diagnosis.

Then, the compounds of this invention shown by formula (I) described above will be explained below in detail. That is, Q in formula (I) is a moiety having an active methylene residue or active methine residue and is preferably a moiety which causes an oxidative coupling reaction with the oxidized product of the hydrogen donor (i.e., a coupler moiety). More preferably, a so-called two-equivalent coupler moiety (for example, an active methylene group or active methine group of a four-equivalent coupler from which a hydrogen atom is removed) used in the field of photographic chemistry is used.

Practical examples of Q are coupler moieties (i.e., yellow coupler, magenta coupler, or cyan coupler moieties) forming yellow, magenta, or cyan dyes by causing a coupling reaction with the oxidized product of a hydrogen donor such as an N,N-dialkyl-p-phenylenediamine; so-called "straight chain" colorless coupler moieties; and uncolored coupler moieties having a cycloketone or cycloimine skeleton.

Couplers used as the coupler moiety Q in this invention are described in, for example, *The Theory of the Photographic Process*, 4th ed., pages 354 to 362, edited by T. H. James (published by Macmillan Publishing Co., Inc. in 1977): British Patent No. 1,038,331; West German Patent No. 1,124,356; U.S. Pat. No. 3,227,550; etc.

For example, a moiety represented by the following formula (M) is particularly useful as the magenta coupler moiety:

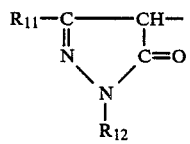

Formula (M):

wherein $R_{11}$ represents an alkyl group having 1 to 10 carbon atoms which is selected from a primary, secondary and tertiary alkyl groups (e.g., a methyl group, an ethyl group, a propyl group, an n-butyl group, a tert-butyl group, a hexyl group, a 2-hydroxyethyl group, a 2-phenylethyl group, etc.), an aryl group having 6 to 10 carbon atoms (e.g., a naphthyl group, a phenyl group, a 2,4,6-trichlorophenyl group, a 2-chloro-4,6-dimethylphenyl group, a 2,6-dichloro-4-methoxyphenyl group, a 4-alkylaminophenyl group (preferably containing the alkyl moiety having 1 to 4 carbon atoms), a 4-trifluoromethylphenyl group, a 3,5-dibromophenyl group, a 4-carboxyphenyl group, a 2-methylphenyl group, a 4-sulfamoylphenyl group, a 3,5-dicarboxyphenyl group, a 4-sulfophenyl group, etc.), a heterocyclic residue (e.g., a 5- and/or 6-membered ring residue containing nitrogen or oxygen, etc. as a heterocyclic atom; more specifically, a quinolinyl group, a pyridyl group, a benzofuranyl group, an oxazolyl group, etc.), an amino group which may optionally be substituted with an alkyl group having 1 to 8 carbon atoms, an aryl group having 6 to 10 carbon atoms, an aralkyl group having 7 to 18 carbon atoms, etc. (e.g., a methylamino group, a diethylamino group, a dibutylamino group, a phenylamino group, a tolylamino group, a 4-(3-sulfobenzamino)anilino group, a 2-chloro5-amino group, an aminoanilino group, a 2-chloro-5-alkoxycarbonylanilino group (preferably containing the alkoxy moiety having 1 to 4 carbon atoms), a 2-trifluoromethylphenylamino group, a 3,5-dicarboxyphenylamino group, a 5-carboxy-2-methoxyphenylamino group, a 2-methoxy-5-(N-methyl)sulfamoylphenylamino group, a 3-sulfamoylphenylamino group, a 5-carboxy-2-chlorophenylamino group, etc.), a carbonamido group (e.g., an ethylcarbonamido group, an alkylcarbonamido group (preferably containing the alkyl moiety having 1 to 10 carbon atoms), an arylcarbonamido group (preferably containing the aryl moiety having 6 to 10 carbon atoms), a benzothiazolylcarbonamido group, etc.), a sulfonamido group (e.g., a methanesulfonamido group, a benzenesulfonamido group, etc.), a ureido group (e.g., an alkylureido group (preferably containing the alkyl moiety having 1 to 10 carbon atoms), an arylureido group (preferably containing the aryl moiety having 6 to 10 carbon atoms), a heterocyclic ureido group such as a 5- or 6-membered cyclic group containing a nitrogen atom, a sulfur atom or an oxygen atom as a hetero atom, more specifically, a benzofuranyl group, a naphthoxazolyl group, a quinolinyl group, etc.), etc.), an alkoxy group having 1 to 10 carbon atoms (e.g., a methoxy group, an ethoxy group, etc.), a carboxyl group, a sulfo group, etc.; and $R_{12}$ represents a hydrogen atom, an aryl group having 6 to 10 carbon atoms in total (e.g., a naphthyl group, a phenyl group, a 2,4,6-trichlorophenyl group, a 2-chloro-4,6-dimethylphenyl group, a 2,6-dichloro-4-methoxyphenyl group, a 4-alkylaminophenyl group containing the alkyl moiety having 1 to 4 carbon atoms, a 4-trifluoromethylphenyl group, a 3,5-dibromophenyl group, a 4-carboxyphenyl group, a 2-methylphenyl group, a 4-sulfamoylphenyl group, a 3,5-dicarboxyphenyl group, a 4-sulfophenyl group, etc.), a heterocyclic group (e.g., a 5- and/or 6-membered cyclic group containing a nitrogen atom or an oxygen atom as a hetero atom, more specifically, a benzofuranyl group, a naphthoxazolyl group, a quinolinyl group, etc.), an alkyl group having 1 to 8 carbon atoms (e.g., an ethyl group, a benzyl group, a 2-cyanopropyl group, a 2-carboxypropyl group, etc.), etc.

Representative examples of the coupler moiety represented by formula (M) include:

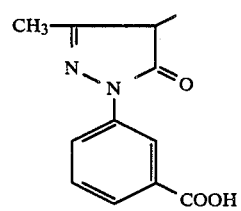

M-1

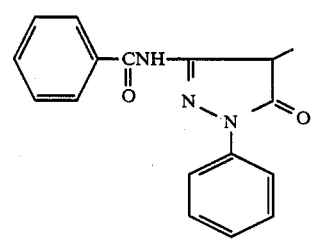

M-2

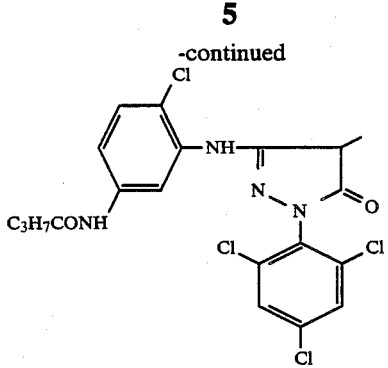
M-3

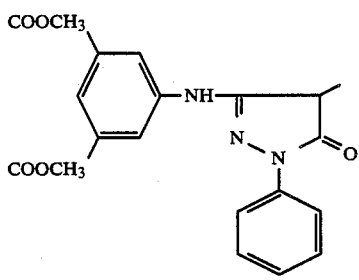
M-4

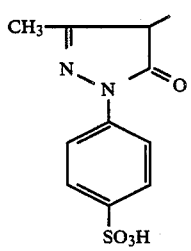
M-5

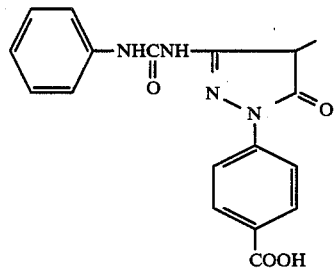
M-6

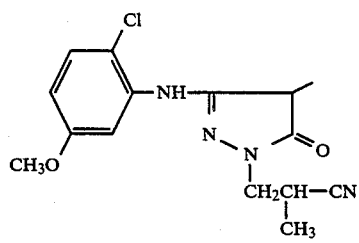
M-7

As the yellow coupler moiety, a moiety represented by the following formula (Y):

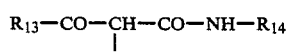  (Y)

is useful: in the formula, $R_{13}$ represents a primary alkyl group, a secondary alkyl group or a tertiary alkyl group having 1 to 10 carbon atoms (e.g., a tert-butyl group, a 1,1-dimethylpropyl group, a 1,1-dimethyl-1-ethylthiomethyl group, a 1,1-dimethyl-1-(4-methoxyphenoxy)- methyl group, etc.), an aryl group having 6 to 10 carbon atoms (e.g., a phenyl group, an alkylphenyl group containing the alkyl moiety of 1 to 4 carbon atoms, a 3-methylphenyl group, a 2-methoxyphenyl group, a 4-methoxyphenyl group, a halophenyl group (as the halogen substituent, a chlorine atom, a bromine atom, a fluorine atom, etc.), a 2-halo-5-alkamidophenyl group containing the alkyl moiety having 1 to 4 carbon atoms (as the halogen substituent, a chlorine atom, a bromine atom, a fluorine atom, etc.), a 2-methoxy-5-alkamidophenyl group containing the alkyl moiety having 1 to 4 carbon atoms, a 2-chloro-5-sulfonamidophenyl group, a 3-carboxyphenyl group, etc.), an amino group which may optionally be substituted with an alkyl group having 1 to 4 carbon atoms, an alkoxy group having 1 to 4 carbon atoms or an aryl group having 6 to 10 carbon atoms (e.g., an anilino group, a p-methoxyanilino group, a 3,5-dicarboxyanilino group, a butylamino group, etc.); and $R_{14}$ represents an aryl group having 6 to 10 carbon atoms (e.g., a 2-chlorophenyl group, a 2-halo-5-alkylamidophenyl group containing the alkyl moeity having 1 to 4 carbon atoms, a 2-methoxyphenyl group, a 2-ethoxyphenyl group, a 3,5-dimethoxycarbonylphenyl group, a 3,5-dicarboxyphenyl group, a 5-ethoxycarbonyl-2-methoxyphenyl group, a 5-carboxy-2-methoxyphenyl group, a 5-methoxycarbonyl-2-chlorophenyl group, a 5-carboxy-2-chlorophenyl group, a 4-sulfophenyl group, a 3-carboxy-4-hydroxyphenyl group, a 3-(N-carboxymethyl)sulfamoylphenyl group, a 5-carboxy-2-methoxyphenyl group, a 3-carboxy-5-methanesulfonylaminophenyl group, a 5-carboxy-2-hydroxyphenyl group, a 3-(N(2-carboxyethyl)sulfamoylphenyl group, a 3,5-disulfophenyl group, etc.).

Representative examples of the coupler moiety represented by formula (Y) include the following moieties:

[Structures Y-1, Y-2, Y-3, Y-4 shown]

-continued

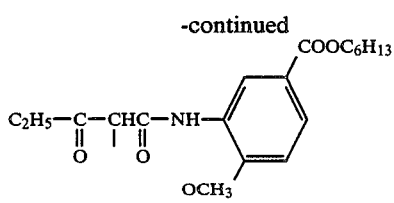 Y-5

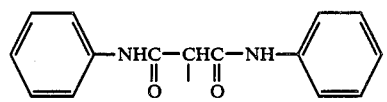 Y-6

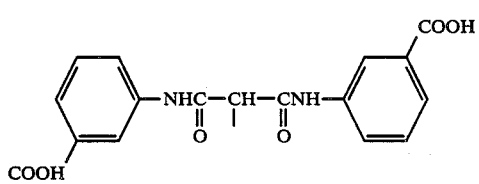 Y-7

As the cyan coupler moiety, coupler residues represented by the following formula (C-1), (C-2) or (C-3) are useful.

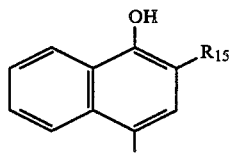 (C-1)

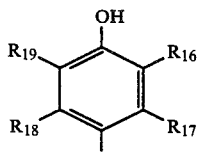 (C-2)

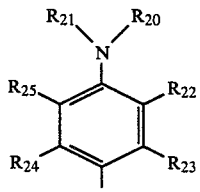 (C-3)

wherein $R_{15}$ represents, for example, a carbamoyl group (e.g., an N-alkylcarbamoyl group containing the alkyl moiety having 1 to 10 carbon atoms, an N,N-dialkylcarbamoyl group containing the alkyl moiety having 2 to 10 in total, an N-phenylcarbamoyl group, an N-arylcarbamoyl group containing the aryl moiety having 6 to 10 carbon atoms, an N-alkyl-N-arylcarbamoyl group having 7 to 10 carbon atoms in total, a heterocyclic carbamoyl group such as an N-benzothiazolylcarbamoyl group, etc.), a sulfamoyl group (e.g., an N-alkylsulfamoyl group containing the alkyl moiety having 1 to 10 carbon atoms, an N,N-dialkyl sulfamoyl group having 2 to 10 carbon atoms in total, an N-phenylsulfamoyl group, an N-arylsulfamoyl group having 6 to 10 carbon atoms, an N-alkyl-N-arylsulfamoyl group having 6 to 10 in total, a heterocyclic sulfamoyl group, etc.), an alkoxycarbonyl group containing the alkoxy moiety having 1 to 10 carbon atoms, an aryloxycarbonyl group containing the aryl moiety having 6 to 10 carbon atoms, etc. In the groups above and hereafter, the moiety of an alkyl nature generally has 1 to 10 carbon atoms, preferably 1 to 4 carbon atoms and the moiety of an aryl nature generally has 6 to 10 carbon atoms, and the heterocyclic moiety is a heterocyclic group containing at least one hetero atom such as nitrogen, oxygen or sulfur, unless otherwise indicated.

$R_{16}$ represents an alkyl group (e.g., a methyl group, an ethyl group, a propyl group, an n-butyl group, a tert-butyl group, a hexyl group, a 2-hydroxyethyl group, a 2-phenylethyl group, etc.), an aryl group (e.g., a naphthyl group, a phenyl group, a 2,4,6-trichlorophenyl group, a 2-chloro-4,6-dimethylphenyl grup, a 2,6-dichloro-4-methoxyphenyl group, a 4-alkylaminophenyl group containing the alkyl moiety having 1 to 4 carbon atoms, a 4-trifluoromethylphenyl group, a 3,5-dibromophenyl group, a 4-carboxyphenyl group, a 2-methylphenyl group, a 4-sulfamoylphenyl group, a 3,5-dicarboxyphenyl group, a 4-sulfophenyl group, etc.), a heterocyclic group (e.g., a 5- or 6-membered ring residue containing nitrogen, oxygen, etc. as a hetero atom; more specifically, a quinolinyl group, a pyridyl group, a benzofuranyl group, an oxazolyl group, etc.), an amino group (an amino group, an alkylamino group, an arylamino group, etc.), a carbonamido group (e.g., an alkylcarbonamido group, an arylcarbonamido group, etc.), a sulfonamido group, a sulfamoyl group (an alkylsulfamoyl group, an arylsulfamoyl group, etc.), a carbamoyl group, etc.

$R_{17}$, $R_{18}$ and $R_{19}$ represent the same groups as defined for $R_{16}$, a halogen atom (e.g., a bromine atom, a chlorine atom, etc.) as described above, an alkoxy group (e.g., a methoxy group, an ethoxy group, a butoxy group, etc.), or the like. Further, $R_{18}$ and $R_{19}$ may combine to form a heterocyclic ring such as a pyridine ring, a pyrole ring, a pyridone ring, an oxazine ring, etc.

$R_{20}$ and $R_{21}$ represent a lower alkyl group having 1 to 5 carbon atoms (e.g., a methyl group, an ethyl group, an ethyl group, a butyl group, etc.), a hhydroxyalkyl group having 1 to 5 carbon atoms (e.g., a methoxy group, an ethoxy group, a butoxy group, etc.), a cyanoalkyl group having 1 to 5 carbon atoms, an acylaminoalkyl group having 1 to 5 carbon atoms, etc.

$R_{22}$, $R_{23}$, $R_{24}$ represent a hydrogen atom or an alkyl group having 1 to 5 carbon atoms (preferably a lower alkyl group having 1 to 4 carbon atoms; specifically a methyl group, an ethyl group, a propyl group, an n-butyl group, a tert-butyl group, etc.), etc.

Representative examples of the coupler moieties represented for formula (C-1) include the following moieties.

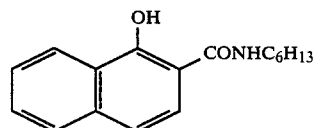 C-1-1

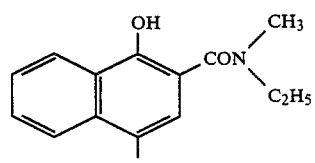 C-1-2

-continued

C-1-3: 1-hydroxy-2-(benzothiazol-2-ylcarbamoyl)-4-methylnaphthalene

C-1-4: 1-hydroxy-2-(pentyloxycarbonyl)-4-methylnaphthalene

C-1-5: 1-hydroxy-2-(N-ethyl-N-phenylcarbamoyl)-4-methylnaphthalene

C-1-6: 1-hydroxy-2-(N-methylsulfamoyl)-4-methylnaphthalene

Representative examples of the coupler moieties represented by formula (C-2) include the following:

C-2-1
C-2-2
C-2-3
C-2-4
C-2-5
C-2-6: 8-hydroxy-5-methylquinoline
C-2-7: 2-hydroxy-5-methyl-N-phenylbenzamide Representative examples of the coupler moieties represented by formula (C-3) include the following:

C-3-1: N,N-diethyl-3-methyl-4-methylaniline derivative
C-3-2: N,N-bis(2-hydroxyethyl)-4-methylaniline
C-3-3: N-ethyl-N-(2-hydroxyethyl)-4-methylaniline
C-3-4: N-ethyl-N-(2-methylsulfonamidoethyl)-3-methyl-4-methylaniline
C-3-5: N-ethyl-N-(2-acetamidoethyl)-3-methyl-4-methylaniline -continued

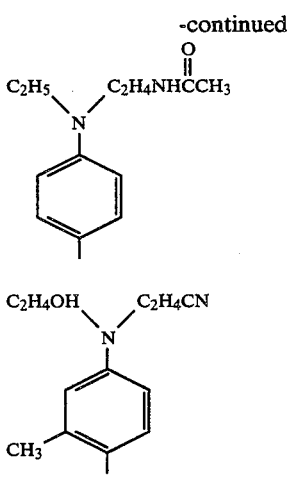
C-3-6

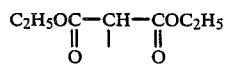
C-3-7

Of non-color forming couplers, examples of so-called "straight chain" couplers include those as described in, e.g., Japanese patent application (OPI) No. 22514/61 (or DAS 1,547,640) and on the other hand, examples of couplers containing a cycloketone or cycloimine skeleton include those as described in, e.g., Japanese patent application No. 31480/75 (corresponding to British Patent No. 1,547,377).

In addition, pyrazolo[2,3-a]benzimidazole type two equivalent coupler moieties as disclosed in U.S. Pat. No. 3,369,897 and Japanese patent application (OPI) No. 26541/76, two-equivalent coupler moieites of hetero ring-substituted acetic acid derivative type as disclosed in Japanese patent applications Nos. 159255/75 and 30591/75 (corresponding to British Patent No. 1,504,094) and further two-equivalent couplers of naphthosulfonic acid type are also useful.

Further, 1,3-diketones such as acetylacetone or acylacetic acid esters can also be employed.

Specific examples of such coupler moities, Q, i.e., coupler moieties Q other than formulae (M), (Y), (C-1), (C2) and (C-3) include the following:

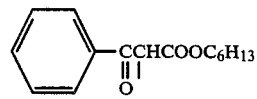
A-1

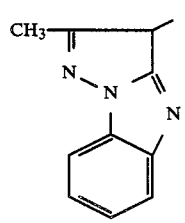
A-2

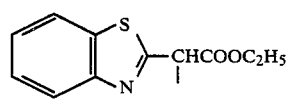
A-3

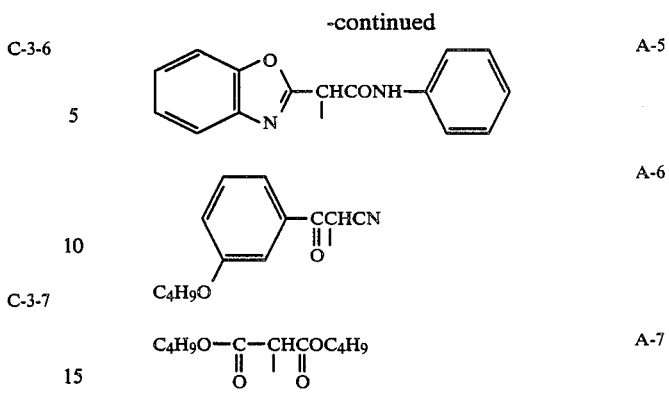
A-4

-continued

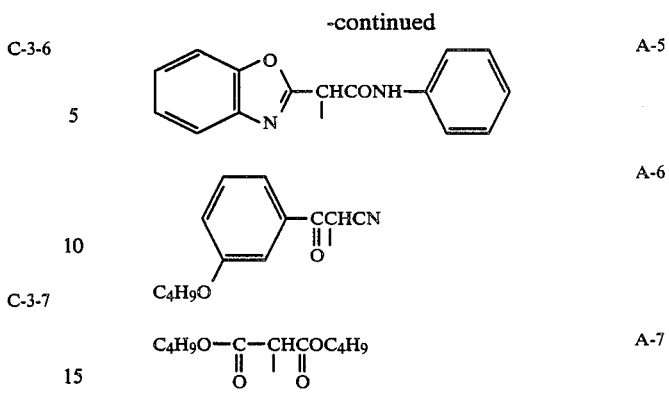
A-5

A-6

A-7

Any moieties can be employed as long as Fl in formula (I) is a compound with does not emit fluoroescence or strong fluorescence when Fl is bonded to moiety Q but capable of emitting, after dissociation, fluorescence by excitement of light which Fl absorbs.

Further, Fl in formula (I) of the present invention is bonded to Q by the following chemical structure contained in its moiety.

—O—   B-1

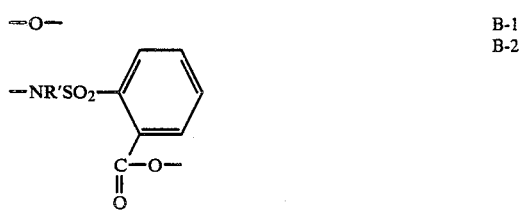
B-2 wherein R' represents a lower alkyl group having 1 to 4 carbon atoms such as a methyl group, an ethyl group, a propyl group, a butyl group, etc.

—O—C—O—   B-3
    ‖
    O

—O—C—NH—   B-4
    ‖
    O

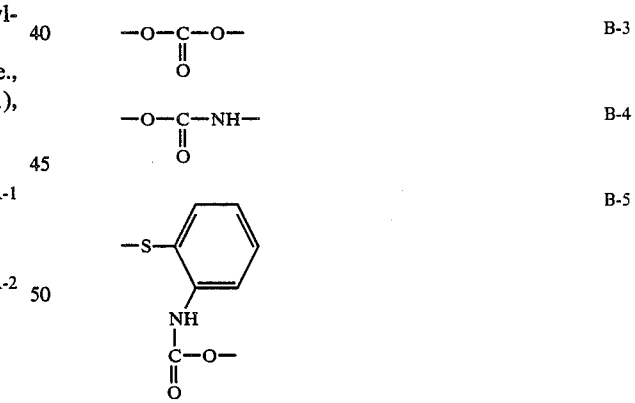
B-5 etc.

Fl having the chemical structure portion as described above is released from Q at the time of the attack of an oxidized hydrogen donor (e.g., quinonediimine) followed by the formation of an azomethine dye so that the aforesaid chemical structure moiety is converted into —OH or —NH$_2$ and becomes a compound emitting fluorescence.

In this case, carbon dioxide, a saccharin type compound or a thiazolinone derivative is sometimes released, depending upon Fl used. For example, when Fl is bonded through, e.g., B-2 described above, a compound of saccharin type is released; likewise, carbon dioxide is released in the case of B-3 and B-4, and in the case of B-5, a compound of thiazolinone type is released.

Representative examples of preferred chemical structures as Fl are those represented by the following formula:

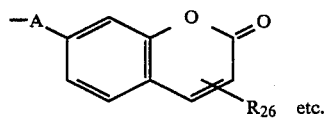 (F1-1)

In the formula described above, $R_{26}$ represents a hydrogen atom, an alkyl group having 1 to 10 carbon atoms (e.g., a methyl group, an ethyl group, a propyl group, an n-butyl group, a tert-butyl group, a hexyl group, a 2-hydroxyethyl group, a 2-phenylethyl group, etc.), an aryl group having 6 to 10 carbon atoms (e.g., a naphthyl group, a phenyl group, a 2,4,6-trichlorophenyl group, a 2-chloro-4,6-dimethylphenyl group, a 2,6-dichloro-4-methoxyphenyl group, a 4-alkylaminophenyl group, a 4-trifluoromethyl group, a 3,5-dibromophenyl group, a 4-carboxyphenyl group, a 2-methylphenyl group, a 4-sulfamoylphenylgroup, a 3,5-dicarboxyphenyl group, a 4-sulfophenyl group, etc.).

Repesentative examples of substances capable of emitting fluorescence, represented by formula (I), Q-Fl, which are employed in accordance with the present invention are shown below but the present invention is not limited only to these compounds.

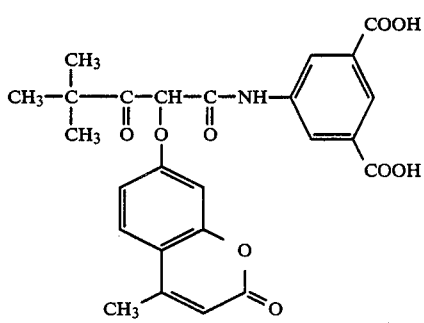 (I-1)

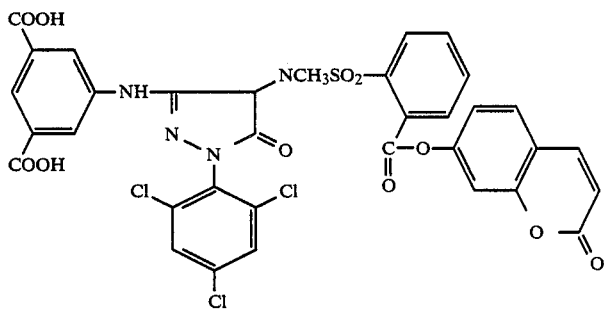 (I-2)

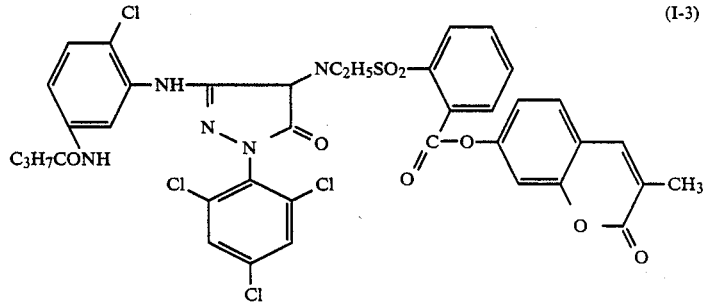 (I-3)

-continued
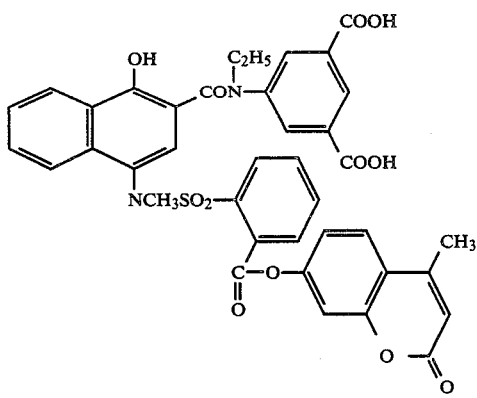
(I-4)
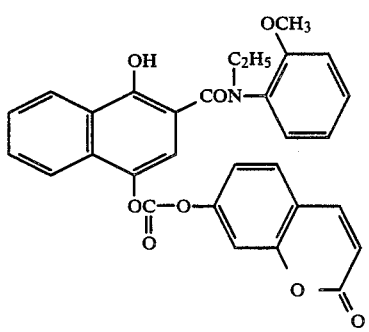
(I-5)
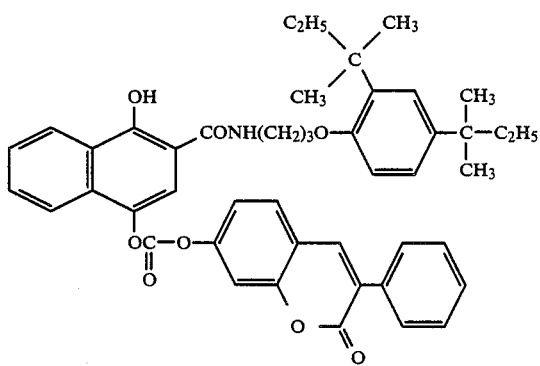
(I-6)
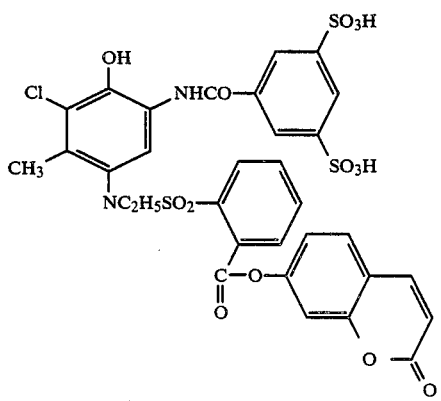
(I-7)

-continued
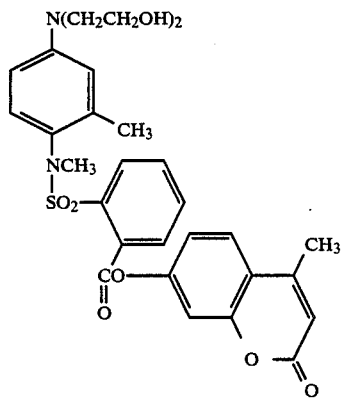 (I-8)
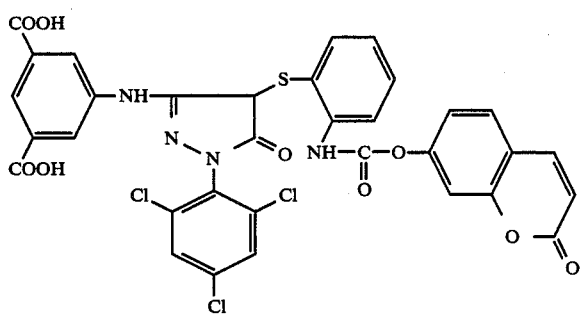 (I-9)
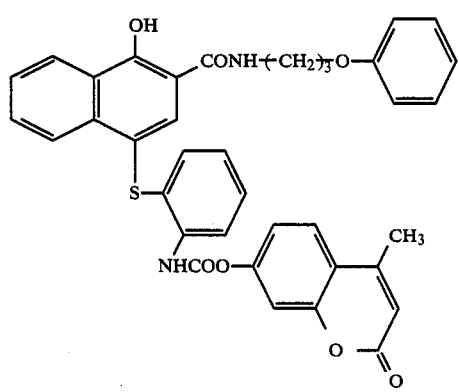 (I-10)
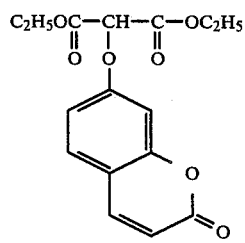 (I-11)
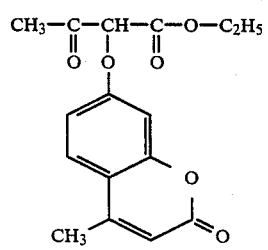 (I-12)

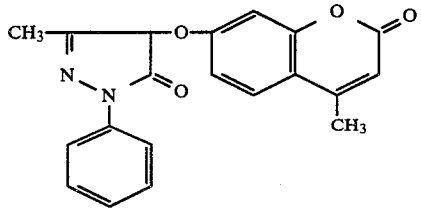

(I-13)

-continued

Compounds represented by formula (I), Q-Fl, can easily be synthesized using commercially available compounds—which correspond to fluorescing moieties (Fl)—as starting materials by applying known methods for synthesizing two-equivalent couplers thereto. Such known methods for synthesis are described in Japanese patent application (OPI) Nos. 13342/75, 159336/75, 117032/76 and 46828/76. U.S. Pat. Nos. 3,737,316 and 3,253,924, etc.

Next, syntheses of representatives among compounds represented by formula (I) are shown below. Compounds that are not specifically shown below can be easily prepared in accordance with Synthesis Examples 1 to 4.

Synthesis Example 1 (synthesis of Compound I-1)

In 35 ml of methylene chloride, 3.35 g (10 mmole) of α-pivaloyl-3,5-dicarbomethoxyacetanilide prepared by the method described in German Patent No. 1,124,356 was dissolved. To the resulting solution, 1.8 g. (11.3 mmoles) of bromine was dropwise added at 5° C. under ice-cooling to lead to an α-bromo derivative. After this solution of the α-bromo compound was washed with saturated saline and water, the solution was dropwise added to a solution composed of 4.14 g. (23.5 mmoles) of 4-methylumbelliferone, 3.1 ml. of triethyl amine, 10 ml. of methylene chloride ad 5 ml. of N,N-dimethylformamide (DMF) at 18° C. under water-cooling. After washing the reaction mixture with an aqueous solution of 1N sodium hydroxide, 1N hydrochloric acid and a 1% aqueous solution of sodium hydrogen carbonate, the reaction mixture was dried over anhydrous sodium sulfate. Methylene chloride was removed by distillation and the residue was recrystallized from a solvent mixture of acetonitrile/methanol to give 4.55 g. (yield 89.5%) of α-pivaloyl-α-4'-methylumbelliferyl-3,5-dicarbomethoxyacetanilide having a melting point of 254° to 256° C. In 30 ml. of methanol of 2.55 g. (5 mmoles) of this dimethyl ester was suspended. A solution of 0.6 g. (15 mmoles) of sodium hydroxide in 15 ml. of water was added to the suspension. After reacting at 0° C. for 1.5 hour, 4.5 ml. of conc. hydrochloric acid was added to the reaction mixture and the precipitate formed was taken up by filtration. After washing with water and air-drying, the precipitate was recrystallized from acetic acid to give 2.05 g. (yield 85.3%) of desired compound (I-1): m.p. 267° C. (decomposed).

Synthesis Example 2 (synthesis of Compound I-12)

In 40 ml. of methylene chloride and 17 ml. of DMF, 17.6 g. (0.1 mole) of 4-methylumbelliferone was suspended and 14 ml. of triethylamine was further added to the suspension to form a homogenous solution. The solution was cooled with flowing water and a solution of 16.5 g. (0.1 mole) of ethyl α-chloroacetoacetate in 10 ml. of methylene chloride was dropwise added to the solution over about 30 mins. while stirring. Thereafter, stirring was continued for further 24 hrs. at 30° C. Then, the reaction mixture was washed with water three times followed by drying the methylene chloride solution over anhydrous sodium sulfate. After drying, methylene chloride was removed by distillation under reduced pressure and 50 ml. of ethanol was added to the residue. When the mixture was stirred at room temperature, Compound I-12, which was a desired product, was precipitated out. The crylstals were filtered, washed with ethanol and air-dried.

Yield 21.5 g. (70.7%), m.p. 105°-106° C.

Synthesis Example 3 (synthesis of Compound I-13)

To 15.2 g. (0.05 mole) of Compound I-19 and 5.4 g. (0.05 mole) of phenylhydrazine, 250 ml. of ethanol was added and the mixture was refluxed for 3 hrs. while stirring. After cooling to room temperature, ethanol was removed by distillation under reduced pressure. The residue was crystallized from ethyl acetate:hexane=1:1 to obtain desired compound I-13.

Yield 10.6 g. (60.9%), m.p. 163°-165° C.

Synthesis Example 4 (synthesis of Compound I-8)

In 150 ml. of N,N-dimethylacetamide, 11.2 g. (0.05 mole) of N,N-bis(2-hydroxyethyl)-N'-methyl-3-methyl-p-phenylenediamine and 16.9 g. (0.05 mole) of 2-(4-methylcoumarin- 7-oxycarbonyl)benzenesulfonyl chloride were dissolved under nitrogen flow and 5 ml. of pyridine was dropwise added thereto at 5° C. under ice-cooling. After completion of the dropwise addition, stirring was continued for 2 hr. at room temperature. The reaction mixture was poured into diluted hydrochloric acid and the formed crystals were filtered followed by washing with water and drying. The crude crystals were recrystallized from ethanol to give desired compound I-8.

Yield 22.3 g. (78.8%), m.p. 187°-190° C.

Hydrogen donors which can be used in the present invention are hydrogen donors capable of attacking the site of Q-Fl bond of formula (I). The term "hydrogen donor" as used herein refers to a compound which, upon the reaction with hydrogen peroxide and a peroxidase, gives hydrogen to hydrogen peroxide to thereby reduce hydrogen oxide to water and is itself oxidized. Hydrogen donors are preferably compounds represented by the following formula (II):

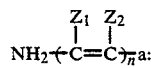   Formula (II)

wherein a represents a hydroxyl group, an amino group, —NHR, —NHR' (wherein R and R' represent an akyl group having 1 to 5 carbon atoms, a cycloalkyl group having 3 to 6 carbon atoms, a hydroxyalkyl group having 1 to 5 carbon atoms, an acylaminoalkyl group having 1 to 5 carbon atoms (e.g., a methanesulfonylaminoalkyl group, an acetylaminoalkyl group, or R and R' may combine to form a ring such as morpholine or piperidine).

$Z_1$ and $Z_2$ represent a hydrogen atom, an alkyl group having 1 to 5 carbon atoms (e.g., a methyl group, an ethyl group, etc.), an alkoxy group having 1 to 5 carbon atoms a halogen atom (e.g., a chlorine atom, a bromine atom, a fluorine atom, etc.), a carboxyl group, a methanesulfonyl group, a phenyl group, etc.; $Z_1$ and $Z_2$ may combine together to form a cycloalkene, an aromatic ring or a heterocyclic ring and specific examples thereof include a benzene ring, a pyrazole ring, a naphthalene ring, etc.

n represents a positive integer and generally 1 to 5, preferably 1 or 2.

Representative examples of hydrogen donors which can be employed in the present invention are 4-aminoantipyrine, p-aminophenol derivatives, N,N-dialkyl-p-phenylenediamine derivatives, etc.

In addition, hydrogen donors as described in L.F.A. Mason, *Photographic Processing Chemistry*, pages 226 to 229 (1966), published by Focal Press, T. H. James, *The theory Of The Photographic Process*, 4th ed., pages 311 to 320, published by Macmillan Publishing Co., Ltd., U.S. Pat. Nos. 2,192,015 and 2,592,364, Japanese patent application (OPI) No. 64933/63, etc.

Specific examples of hydrogen donors are shown below but the present invention is not deemed to be limited only to these compounds.

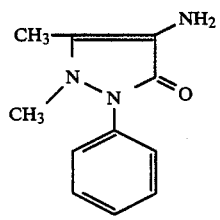 II-1

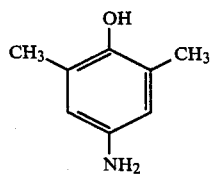 II-2

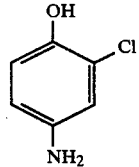 II-3

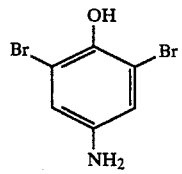 II-4

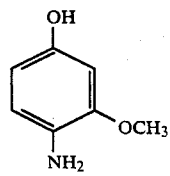 II-5

-continued

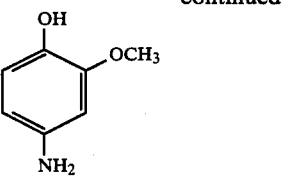 II-6

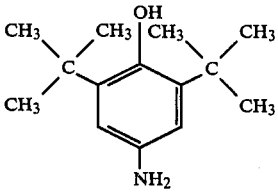 II-7

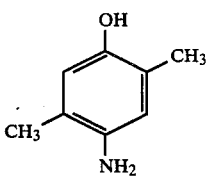 II-8

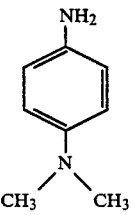 II-9

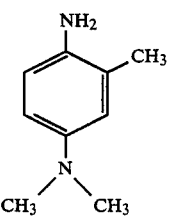 II-10

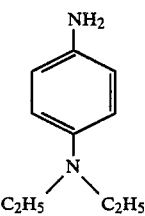 II-11

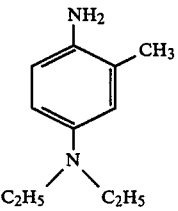 II-12

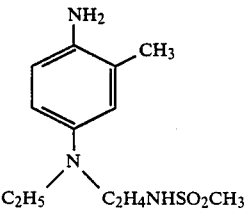 II-13

II-14 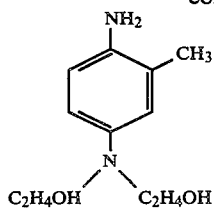

II-15 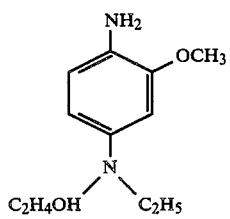

II-16 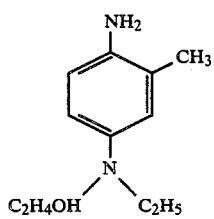

II-17 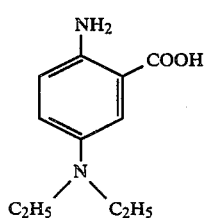

II-18 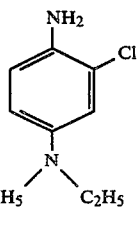

II-19 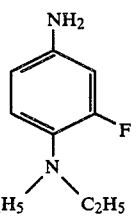

and mineral acid salts of organic salts thereof.

The peroxidase which is other effective component of the reagent for assaying a specific component of this invention is a catalyst for the oxidation reaction of the hydrogen donor by hydrogen peroxide and peroxidases of any origin can be used in this invention.

Each effective component of the reagent of this invention is prepared separately as a powder thereof or a solution in water or a buffer solution, and at use, i.e., at quantitative analysis, they are used as a desired combination of these components, a mixture of these powdery components, or a solution of the components in water or a buffer solution. In the case of using the components as a solution, these components may be dissolved in water or a buffer solution simultaneously or in a desired addition order.

The reaction (fluorescing reaction) of the reagent of this invention and hydrogen peroxide is shown by the following equation;

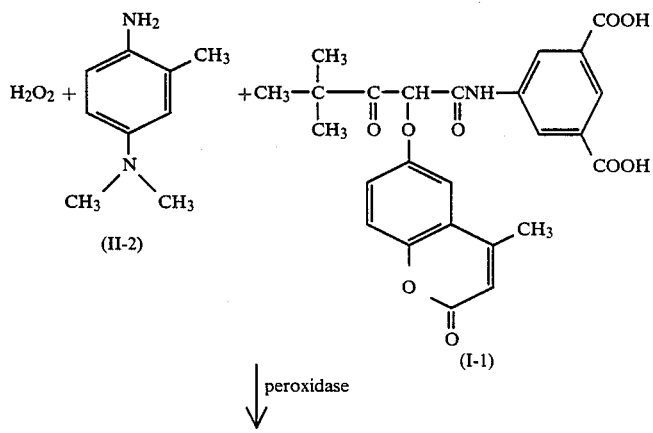

↓ peroxidase

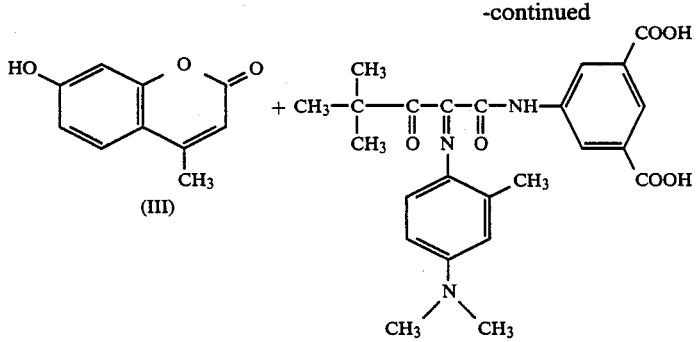

By the foregoing reaction, the fluorescing material (4-methylumbelliferone in this case) of formula (III) is formed and by measuring the fluorescence from the fluorescing material of formula (III) thus formed, the determination of hydrogen peroxide can be performed.

By using the reagent for assaying a specific component of this invention, it becomes possible to quantitatively determine hydrogen peroxide at a high accuracy from a sample containing hydrogen peroxide in an optional concentration.

The method of quantitative assay of this invention can be performed, for example, as follows: The fluorescing material of formula (I), the hydrogen donor and the peroxidase as a reaction catalyst in the above-described formed are added to a sample, simultaneously or in optional order. The mixture is reacted for 1 to 60 minutes at a temperature of 5° to 40° C. and a pH 3.0 to 7.0. The reaction mixture containing a fluorescing material thus formed (the fluorescing material of Fl—OH type is, for example, a umbelliferone derivative and that of Fl—NH₂ type is, for example, a 7-aminocoumarin derivative, etc.) is excited at a pH of 8.0 to 10.5 using light of wavelengths of 280 to 400 nm, and the intensity of the fluorescence in a wavelength of 400 to 500 nm is measured.

The method of this invention is particularly advantageous for the microdetermination of hydrogen peroxide.

It is preferred that the concentration of hydrogen peroxide in a sample be generally 0.02 to 200 ng/ml (total reaction capacity system). In the concentration of hydrogen peroxide, the fluorescing material is used in an amount of 0.50 to 10 μmole/ml, the hydrogen donor in an amount of 1–100 n mole/ml, and the peroxidase in an amount of 0.1 to 1.0 unit/ml (all in total reaction capacity system).

Also, by further combining an oxidase with the effective component of formula (I), the hydrogen donor and the peroxidase in the determination method of this invention, the measurement in a wider range becomes possible. That is, using an oxidase together with the effective components of the determination reagent of this invention in the case that a material to be finally determined forms hydrogen peroxide by the action of the oxidase, it becomes possible to determine various materials by determining hydrogen peroxide. Practically, about urine and body fluid, glucose, uric acid, cholesterol, triglyceride, lactic acid, creatinine, free fatty acid, glutamylpyruvate transaminase, glutamyloxalacetate transaminase, cholinesterase, creatine phosphokinase, lactic acid dehydrogenase, etc., can be measured.

As the oxidase used for the measurement of these materials, there are glucose oxidase, uricase cholesterol oxidase, oxidase L-α-glycerophosphate, oxidase pyruvate, etc. These oxidases may be from any origins and the oxidase may be used as the form of a powder but is preferably used as a solution thereof in water or, in particular, as a buffer solution.

In the case of using an oxidase together with the components of the determination reagent of this invention, hydrogen peroxide may be previously formed by the action of the oxidase but it is preferred to simultaneously perform the formation reaction of hydrogen peroxide and the fluorescing reaction. In this case, the oxidase may be addedd to a sample at any desired period or may be added together with the component of formula (I), the hydrogen donor, or the peroxidase or together with the three effective components. The amount of the oxidase is properly selected according to the kind thereof, the kind of the substrate, and materials contained in the substrate.

The assay method of this invention can be suitably used for the quantitative analysis of hydrogen peroxide in ordinary chemical experiments as well as can be utilized for quantitatively determining an aimed material by assaying hydrogen peroxide finally formed by reacting an oxidase and the material to be assayed as methods of assaying glucose, uric acid, cholesterol, triglyceride, lactic acid, creatine, free fatty acid, glutamylpyruvate transaminase, glutamyloxalacetate transaminase, cholinesterase, creatine phosphokinase, lactic acid dehydrogenase, etc., in urine and body fluid among the clinical inspections using an enzymeimmunoassay method which is being rapidly utilized recently. For example, in the same of assaying glucose, glucose oxidase is reacted with glucose to thereby form gluconic acid and hydrogen peroxide; hydrogen peroxide thus formed is then quantitatively determined using the reagent of the present invention in accordance with the method of the present invention. Also, by combining the effective component of formula (I) as the reagent, the hydrogen donor and hydrogen peroxide, the reagent thus obtained can be used for the quantitative determination of peroxidase, for example, can be utilized for enzyme immunoassay using peroxidase.

Furthermore, the invention can be utilized for the measurement of urines and body fluids of not only human but also various animals such as domestic animals, pets, etc.

Then, the invention will be further described in more detail by the following examples.

EXAMPLE 1

(Quantitative Analysis of hydrogen peroxide)

In 5 ml of high-grade dimethylformamide was dissolved 60 mg of the compound of formula I-1 and to 0.5 ml of the solution was added 50 ml of a 0.1M acetic acid buffer solution. Furthermore, 1.2 mg of the compound of formula II-19 and 5.5 mg of peroxidase (54 units/mg, made by Sigma Co.) were added to the mixture and then the total amount of the resulting mixture was correctly adjusted to 100 ml by the addition of the above-described buffer to provide solution A.

After adding 1 ml of solution A to 0.1 ml of aqueous hydrogen peroxide solutions having various concentrations (0.25 to 1 n mole/ml), each mixture was incubated for 10 minutes at 37° C. This reaction is shown by the following equation.

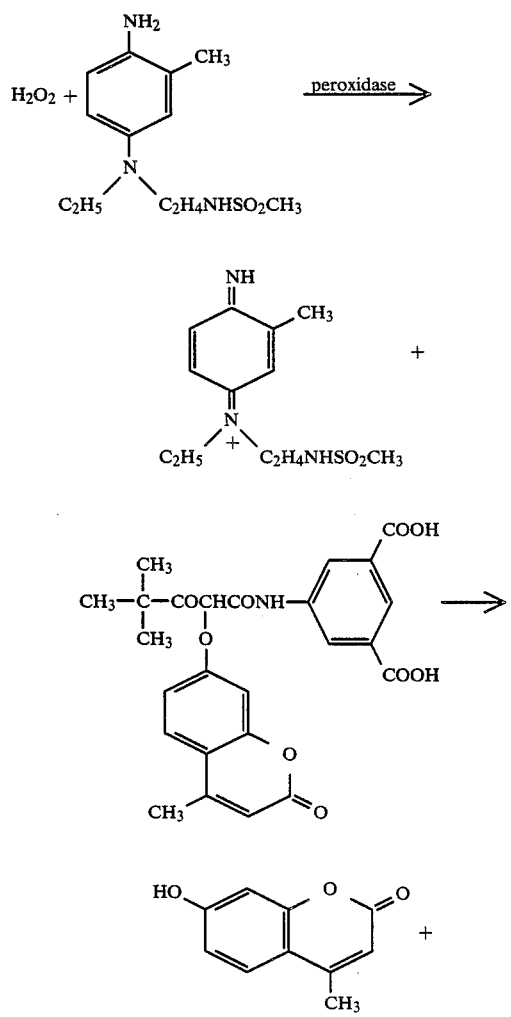

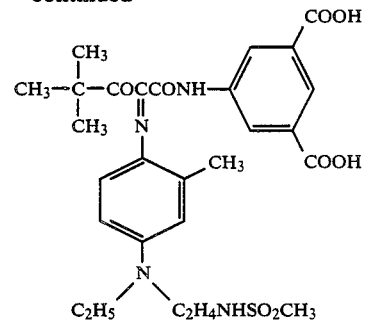

After the incubation was finished, 2.5 ml of a 0.1M glycine NaOH buffer solution having a pH of 10 was added to the incubation product and 4-methylumbelliferone thus formed was measured using a fluorescence photometer at an excitation wavelength of 358 nm and a fluorescence wavelength of 448 nm.

Figure 1:
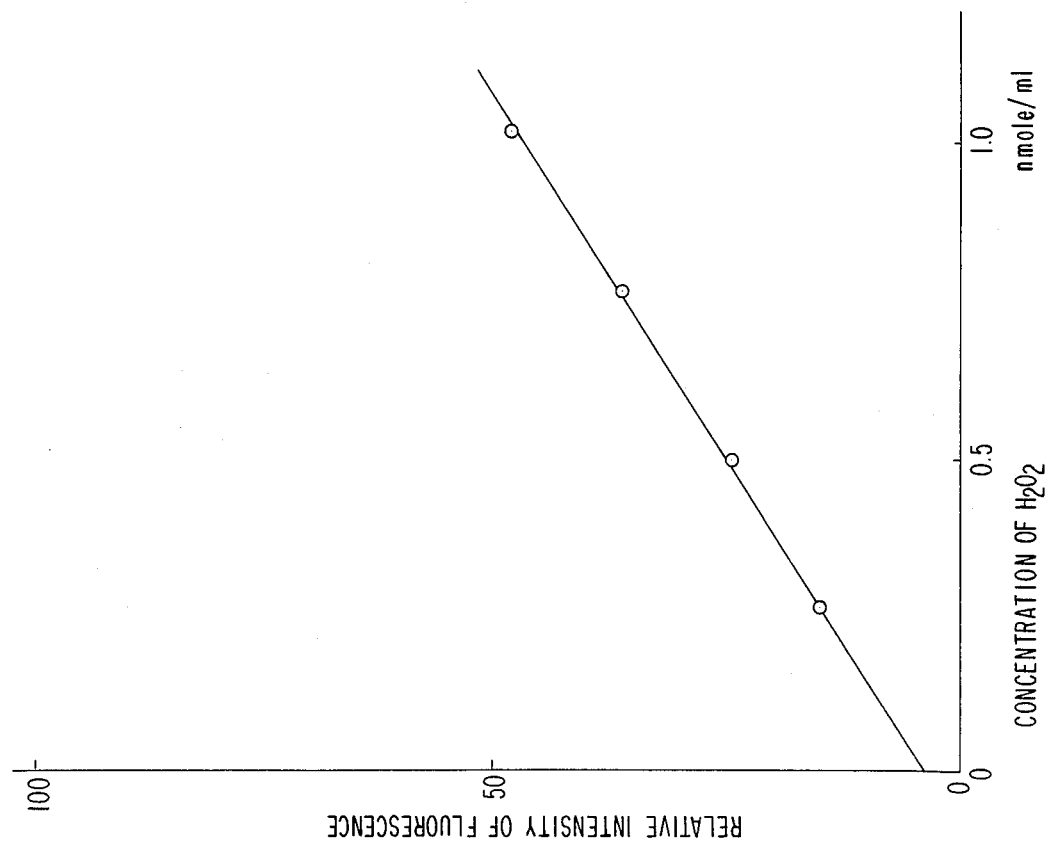
FIG. 1 is a graph showing a calibration curve of hydrogen peroxide obtained in Example 1 and, FIG. 2 is a graph showing a calibration curve of hydrogen peroxide obtained in Example 2.

The relation between the intensity of fluorescence and the amount of hydrogen peroxide obtained by the measurement became linear as shown in FIG. 1, wherein the axis of abscissa stands for the concentration of hydrogen peroxide and the axis of ordinate stands for the relative intensity of fluorescence.

As described above, according to the method of this invention, a sufficient value was obtained even in a low pH range as 5.

EXAMPLE 2

(Quantitative Analysis of hydrogen peroxide)

Following the same procedure as in Example 1 using the compound of formula I-12 and the compound of formula II-19 in place of the compound of formula I-1 used in Example 1, the measurement of aqueous hydrogen peroxide solutions of various concentrations (0.25 to 1 n mole/ml) was performed. Thus, 4-methylumbelliferone formed was measured using a fluorescence photometer at an excitation wavelength of 358 nm and a fluorescence wavelength of 448 nm.

The relation between the intensity of fluorescence and the amount of hydrogen peroxide obtained by the measurement became as shown in FIG. 2, wherein the axis of abscissa stands for the concentration of hydrogen peroxide and the axis of ordinate stands for the relative intensity of fluorescence.

EXAMPLE 3

(Quantitative Analysis of hydrogen peroxide)

Following the same procedure as in Example 1, four kinds of solutions A having different pH were prepared using the buffer solutions having pH 6 and pH 7 shown in Table 1 in place of 50 ml of a 0.1M acetic acid buffer solution of pH 5. Furthermore, 1 ml of each solution A was added to 0.1 ml of an aqueous hydrogen peroxide solution of 0.5 n mole/ml and the mixture was incubated for 10 minutes at 37° C. After the incubation was finished, 2.5 ml of a 0.1M glycine-NaOH buffer solution of pH 10 was added to the incubation product and the intensity of fluorescence was measured in each case. The results are shown in Table 1.

Then, following the same procedure as above using the compound of formula I-3 and the compound of formula II-4 in place of the compound of formula I-12 and the compound of formula II-19, the intensity of fluorescence was measured in each case. These results are shown in Table 1.

On the other hand, according to a conventional method using diacetylfluorescin in place of the compound of this invention, the intensity of fluorescence was measured using each of the buffer solutions as described above and the reaults are shown in Table 1.

TABLE 1

| Reagent | (A)* pH 5 | (B)** pH 6 | pH 7 |
|---|---|---|---|
| I-12 + II-19 | 43.3 | 48.3 | 48.5 |
| I-3 + II-4 | 43.8 | 44.5 | 44.5 |
| Diacetyl-fluorescin | 12.7 | 17.6 | 25.3 |

(A)*: 0.1 M acetate buffer solution
(B)**: 0.1 M phosphate buffer solution

As is understood from the results shown in Table 1, according to the method of this invention, the determination of hydrogen peroxide can be performed at a very high sensitivity in a low pH region of 5 to 7 as compared with conventional method, thereby the measurement fitting to the optimum pH of oxidase becomes possible and thus the measuring accuracy, the simplicity and quickness of operation, and the economical value of the method can be increased.

EXAMPLE 4

(Measurement of cholesterol)

In 5 ml of high-grade dimethylformamide was dissolved 60 ml of the compound of formula I-12. To 0.5 ml of the solution was added 50 ml of a 0.1M phosphoric acid buffer solution of pH 6. Furthermore, 1.2 mg of the compound of formula II-1, 1 mg of cholesterol oxidase (20 units/mg, made by Sigma Co.), and 5.5 mg of peroxidase (54 units/mg, made by Sigma Co.), were added to the mixture and then the total volume of the mixture was accurately adjusted to 100 ml by the addition of the foregoing buffer solution to provide solution A.

To 200 mg of cholesterol was added the foregoing buffer solution to provide 100 ml of the solution and then the solution was further diluted 100 times to provide solution B.

In a test tube was placed 10 μl of solution B and after adding thereto 1 ml of solution A, the mixture was incubated for 10 minutes at 37° C. After the incubation was finished, 2.5 ml of a 0.1M glycine buffer solution of pH 1 was added to the incubation product and 4-methylumbelliferone thus formed was measured using a fluorescence photometer at an excitation wavelength of 358 nm and a fluorescence wavelength of 448 nm. Thus, a fluorescence sensitivity of 55 was obtained.

As described above, according to the method of this invention, a satisfactory value was obtained in a low pH range as 6.

EXAMPLE 5

(Measurement of Glucose)

In 5 ml of high-grade dimethylformamide was dissolved 60 ml of the compound of formula I-3 and to 0.5 ml of the solution was added 50 ml of a 0.1M acetic acid buffer solution of pH 5. Furthermore, 1.2 mg of the compound of formula II-4, 3.3 mg of glucose oxidase (125 units/mg, made by Sigma Co.), and 5.5 mg of peroxidase (54 units/mg, made by Sigma Co.) were added to the mixture and the total volume of the mixture was accurately adjusted to 100 ml by the addition of the foregoing buffer solution to provide solution A.

To 200 mg of glucose was added the foregoing buffer solution to provide 100 ml of the solution and then the solution was further diluted 100 times to solution B.

In a test tube was placed 10 μl of solution B and after adding thereto 1 ml of solution A, the mixture was incubated for 10 minutes at 37° C.

After the incubation was finished, 2.5 ml of a 0.1M glycine-NaOH buffer solution of pH 10 was added to the incubation product and 4-methylumbelliferone thus formed was measured using a fluorescence photometer at an excitation wavelength of 358 nm and a fluorescence wavelength of 448 nm. The sensitivity of fluorescence was 85.

As described above, according to the method of this invention, the satisfactory measurement could be performed at a low pH range as 5.

EXAMPLE 6

(Measurement of Cholesterol)

When the same measurement as in Example 3 was performed using the compound of formula I-11 in place of the compound of formula I-6 and the compound of II-19 in place of the compound of formula II-1 in Example 3, the fluorescence sensitivity of 36 was obtained.

As described above, according to the method of this invention, the preferred measurement as in Example 3 could be performed at a low pH range.

While the invention has been described in detail and with reference to specific embodiments thereof, it will be apparent to one skilled in the art that various changes and modifications can be made therein without departing from the spirit and scope thereof.

What is claimed is:

1. A method of assaying hydrogen peroxide which comprises reacting a sample liquid containing hydrogen peroxide with a reagent kit for assaying hydrogen peroxide and incubating the resulting mixture of the sample liquid and the reagent kit and determining the intensity of fluorescence emitted in proportion to hydrogen peroxide as a result of the incubation, wherein the reagent kit comprises:

(1) a compound having a coupler moiety formed at a coupling size by removing one hydrogen atom from an active methylene group of the formula —CH$_2$— having directly or indirectly bonded thereto an electron withdrawing or electron attracting group, and a fluorescing moiety, which compound is represented by the formula:

Q—Fl wherein Q represents the coupler moiety formed at the coupling site by removing one hydrogen atom from the active methylene group of the formula —CH$_2$—, which coupler moiety is a yellow coupler moiety which causes an oxidative coupling reaction with an oxidized product of a hydrogen donor, which yellow coupler moiety is represented by the formula:

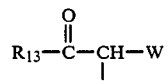

wherein $R_{13}$ represents an alkyl group having 1 to 10 carbon atoms, an aryl group having 6 to 10 carbon atoms or an amino group; and wherein W is

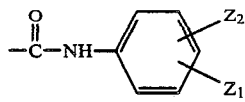

—COOC$_2$H$_5$, —COOC$_6$H$_{13}$, —C≡N or COOC$_4$H$_9$; wherein $Z_1$ and $Z_2$ are from the pairs:

H, —Cl;
—OCH$_3$, —COOC$_2$H$_5$;

—Cl, —NHCCH$_3$;
    ‖
    O

H, H;
—COOH, —COOH;
—OCH$_3$, —COOC$_6$H$_{13}$; or
H, —COOH; and wherein Q is bonded to Fl by an active methine group therein; and Fl represents the fluorescing moiety which emits fluoroescence by being separated from Q, which moiety is represented by the formula:

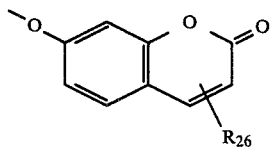

wherein $R_{26}$ is a hydrogen atom, an alkyl group having 1 to 10 carbon atoms or an aryl group having 6 to 10 carbon atoms, wherein Fl is splittable from Q—Fl;

(2) a hydrogen donor and
(3) a peroxidase, and measuring the intensity of the fluorescence emitted from the fluorescing moiety formed by the reaction of hydrogen peroxide, the hydrogen donor and the compound of the formula Q—Fl in the presence of peroxidase.

2. The method of claim 1 wherein said hydrogen donor is represented by the formula:

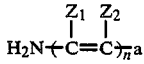

wherein a represents a hydroxyl group, an amino group NHR' or NRR', wherein R and R' each represents an alkyl group, a cycloalkyl group, or an acylaminoakyl group, or R and R' may combine to form a hetero ring $Z_1$ and $Z_2$ of the hydrogen donor compound represent a hydrogen atom, an alkyl group having 1 to 5 carbon atoms, an alkoxy group having 1 to 5 carbon atoms, a halogen atom, a carboxyl, a methanesulfonyl group or a phenyl group or $Z_1$ and $Z_2$ may combine together to form a benzene ring, a pyrazole ring or a naphthalene ring and n represents a positive integer of from 1 to 5.

3. A reagent kit for assaying hydrogen peroxide comprising:

(1) a compound represented by the formula:

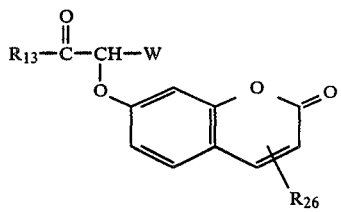

wherein $R_{13}$ is an alkyl group having 1 to 10 carbon atoms, an aryl group having 6 to 10 carbon atoms or an amino group; W represents:

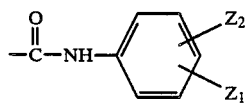

—COOC$_2$H$_5$, —COOC$_6$H$_{13}$, —C≡N or —COOC$_4$H$_9$; wherein $Z_1$ and $Z_2$ of group W are from the pairs:

H, —Cl;
—OCH$_3$, —COOC$_2$H$_5$;

—Cl, —NHCCH$_3$;
    ‖
    O

H, H;
COOH, COOH;
—OCH$_3$, —COOC$_6$H$_{13}$; or
H, —COOH;
and, $R_{26}$ is a hydrogen atom, an alkyl group having 1 to 10 carbon atoms or an aryl group having 6 to 10 carbon atoms;

(2) a hydrogen donor and
(3) a peroxidase.

4. The reagent kit of claim 3 wherein said hydrogen donor is represented by the formula:

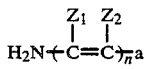

wherein a represents a hydroxyl group, an amino group, —NHR or —NRR', wherein R and R' each represents an alkyl group having 1 to 5 carbon atoms, a cycloalkyl group having 3 to 6 carbon atoms, a hydroxyalkyl group having 1 to 5 carbon atoms, or an acylaminoalkyl group having 1 to 5 carbon atoms, or R and R' may combine to form a morpholino or piperidino ring, $Z_1$ and $Z_2$ of the hydrogen donor cmpound represent a hydrogen atom, an alkyl group having 1 to 5 carbon atoms, a alkoxy group having 1 to 5 carbon atoms, a halogen atom, a carboxyl group, a methanesulfonyl group, or a phenyl group or $Z_1$ and $Z_2$ of the hydrogen donor compound may combine together to form a benzene ring, a pyrazole ring or a naphthalene ring, and n represents a positive integer of from 1 to 5.

5. The reagent kit of claim 3 wherein the —CH— group of said compound has directly or indirectly bonded thereto an electron withdrawing or attracting group selected from the group consisting of a carbonyl group, a cyano group, a halogen atom, a sulfonyl group, a sulfoxide group, a nitro group and an amino group.

* * * * *